United States Patent
Lysen

(12) United States Patent (10) Patent No.: US 6,591,682 B1
(45) Date of Patent: Jul. 15, 2003

(54) DEVICE AND PROCESS FOR SIGNAL ANALYSIS

(75) Inventor: Heinrich Lysen, Garching (DE)

(73) Assignee: Pruftechnik Dieter Busch AG, Ismaning (DE)

(*) Notice: Subject to any disclaimer, the term of this patent is extended or adjusted under 35 U.S.C. 154(b) by 76 days.

(21) Appl. No.: 09/637,581

(22) Filed: Aug. 14, 2000

(51) Int. Cl.[7] .......................... G01N 29/08; G01L 7/00; G01L 11/00

(52) U.S. Cl. ...................... 73/602; 73/597; 73/646; 73/660; 702/56

(58) Field of Search .................. 73/660, 602, 593, 73/659, 587, 579, 597, 598, 646; 702/35, 56

(56) References Cited

U.S. PATENT DOCUMENTS

| | | | |
|---|---|---|---|
| 3,677,072 A | 7/1972 | Weichbrodt et al. | 73/593 |
| 3,842,663 A | 10/1974 | Harting et al. | 73/593 |
| 4,386,526 A | 6/1983 | Roeder | 73/587 |
| 4,455,862 A | 6/1984 | Takeuchi | 73/35.03 |
| 4,884,449 A | 12/1989 | Nishimoto et al. | 73/660 |
| 4,980,844 A * | 12/1990 | Demjanenko et al. | 702/56 |
| 5,109,700 A * | 5/1992 | Hicho | 73/660 |
| 5,144,838 A * | 9/1992 | Tsuboi | 73/579 |
| 5,179,860 A * | 1/1993 | Tsuboi | 73/579 |
| 5,251,151 A | 10/1993 | Demjanencko et al. | 702/56 |
| 5,511,422 A * | 4/1996 | Hernandez | 73/593 |
| 5,602,757 A * | 2/1997 | Haseley et al. | 73/660 |
| 5,648,613 A * | 7/1997 | Kiefer | 73/611 |
| 5,679,900 A | 10/1997 | Smulders | 73/659 |
| 5,804,726 A * | 9/1998 | Geib et al. | 73/593 |
| 5,895,857 A * | 4/1999 | Robinson et al. | 73/660 |
| 6,144,923 A * | 11/2000 | Grosse | 702/56 |
| 6,257,066 B1 * | 7/2001 | Chandler et al. | 73/649 |
| 6,289,735 B1 * | 9/2001 | Dister et al. | 73/579 |
| 6,321,602 B1 * | 11/2001 | Ben-Romdhane | 73/660 |

FOREIGN PATENT DOCUMENTS

EP 0 413 845 2/1991

OTHER PUBLICATIONS

Machine Condition Monitoring: Part 2—The Effects of Noise in The Vibration Signal, C.K. Mechefske, British Journal of NDT, vol. 35., No. 10, Oct. 1993, pp. 574–579.

* cited by examiner

*Primary Examiner*—Helen Kwok
*Assistant Examiner*—Jacques Saint-Surin
(74) *Attorney, Agent, or Firm*—Nixon Peabody LLP; David S. Safran

(57) ABSTRACT

A device for detecting or analyzing machinery damage is used preferably in the determination of defects in roller bearings. Pulse-like machinery or bearing noise acquired by a sensor is converted into special time signals. These time signals correspond to events which are basically periodic in occurrence. The time signals are sent to one, preferably several, classification units depending on the time differences. Before classification, combination of adjacent time signals or events is performed using their pulse heights. The combining is multiplicative or obeys some other bivalent relation. Classification forms a frequency distribution with an abscissa which is divided into time units. Specific characteristics of the frequency distribution provide information on incipient or manifest machinery damage.

22 Claims, 2 Drawing Sheets

DEVICE AND PROCESS FOR SIGNAL ANALYSIS

BACKGROUND OF THE INVENTION

1. Field of the Invention

The invention relates to a device and a process for signal analysis. The signals can be of general form and can be present especially as one-dimensional, particularly time signals. Signals of this type in the area of engineering are derived for example from noise signals, as are caused by running machinery. Another example from the area of engineering is signals which represent a regular machine state, or which are characteristics of a brief or continuing defect. These defects can relate to the machinery itself, or a product produced by this machinery.

2. Description of Related Art

The numerous and varied signal analysis processes of type to which this invention is directed are known. If the ratio between a signal portion of interest and a noise portion is large enough, analysis is usually less difficult. But, it is of special interest and considerable difficulty to extract those signal portions which are strongly adulterated by noise. Likewise, it is of special interest to identify individual signals or those which occur only briefly or sporadically and possibly stochastically when a host of other signals is present at the same time.

For example, it is known that it is extremely difficult to identify bearing noise in a machine when the signal/noise ratio becomes less than a value of roughly 0.25 (compare British Journ. of NDT, Vol. 35 No. 10, p. 574 ft). The use of conventional Fourier analyses has almost no effect in this case.

Furthermore, a device for detecting or analyzing machinery damage of a type to which this invention is also directed, especially for detection of errors on roller bearings, is known from U.S. Pat. No. 3,842,663. This patent explains a standard problem which occurs when machinery or bearing damage is detected. This is based on the fact that the noise periodically emitted by bearing defects or other defective hardware parts is much smaller than regular noise which is produced by this machinery and may be present as solid-borne noise.

The approach presented in U.S. Pat. No. 3,842,663 is based on acquiring machinery noise, such as for example transmission or bearing noise, by means of a suitable detector and converting it into an electrical signal. In this case, the damaged bearing or machine parts produce pulse-like noise portions which preferably excite the natural resonances of this detector. Its electrical output signal is processed by a pre-filter and a demodulator. The resulting signal then corresponds essentially to a pulse series. In this pulse series, an individual pulse represents an individual noise caused by sudden motion components.

In periodically repeated pulses of this type, it is possible to determine an especially pronounced or emerging signal frequency with an output-connected spectral analyzer. This frequency, at a known base frequency of the machinery or certain rpm and characteristics of a bearing, allows a conclusion regarding a defect within the machine or bearing.

U.S. Pat. No. 5,679,900 describes how the aforementioned device can be used by using a switchable filter in a paper-making machine. This document also considers that the machinery defects can be characterized by pulse-like vibration portions compared to regular machinery noise, and that they can be emphasized by suitable vibration sensors and by suitable signal processing against the base noise of the machinery and mechanical assemblies.

But, the described devices and processes are subject to the disadvantage that efficient, and thus expensive, spectral analyzers must be provided for reliable representation of the results obtained or additional complex filter units must be connected on the input side.

In addition, the pulse like vibration portions tend to be characterized by significant amplitude, but of rather little energy content. This is because of their short duration. In terms of energy, such pulse-like vibration portions are likely to be "buried" in background noise and thus difficult to impossible to find.

SUMMARY OF THE INVENTION

The primary object of the invention is to improve the quality of analysis results and to significantly reduce the required effort for detecting machine damage, especially bearing damage, by cost-favorable electronic circuitry or data processing.

Another object of the invention is to make available a device and process for improved signal analysis which is especially suitable for detection of an early stage of incipient bearing or machinery damage.

It is also the object of the invention to devise a device and process by which improved, more effective analysis or detection is possible for recognition of those signal portions which are characterized by only a brief presence in time, i.e., transient signal effects. The process in accordance with the invention can, moreover, be used, for example, for detection of very noisy signals.

The invention is based on the finding that a sampled time signal usually present in digitized form can be interpreted as an ordered set of individual events with an inner correlation which is initially unknown. The invention is furthermore based on the finding that the results of conventional, known correlation analyses can be supplemented and improved by abandoning the practice of combining with one another of sections of these signals which are shifted relative to one another in time. Rather, in accordance with the invention, each individual event (according to the definition above) of a signal to be examined is combined at least once with one or more other individual events, which are separated from each other by a time difference. Then, the results of the individual combinations are sent for classification. In particular, it is of interest according to the invention to provide for classification purposes one such combination in the manner of a distribution which has been formed by summation. The x-axis of this distribution is preferably arranged by time classes. The individual time classes correspond to the time differences so that the results of the individual combinations can be fitted into the distribution using the underlying time differences. It is advantageous for combination of the events to perform multiplications each time. However, for this purpose, other binary logic operations can be used, for example, summation or determining a maximum.

According to one preferred approach of the invention, it is provided that each event be combined with all its predecessors or with those predecessors which are located in its immediate vicinity. According to another approach of the invention, it is provided that each event be combined with any other and the results of the combination likewise be sent for classification.

According to still another implementation of the invention, it is provided that events of predefined "quality"

(i.e. having predefined characteristics) be preselected for constituting a "filtered" signal, consisting of such specific events which then are to be combined with any other, and the results of the combination be sent for classification in a comparable way.

In accordance with the invention, the classification results obtained by a distribution analysis can be evaluated either directly or can be sent for additional analysis. Here, it is especially useful to normalize those extreme values of a resulting frequency distribution by a mapping rule which can be interpreted to relate to an integral multiple of a time difference between two predetermined extreme values. One such extreme value, therefore, belongs to a time class of the distribution which is characterized by a smaller (difference) time value than the time classes of the integral multiple of the first extreme value.

In the direct evaluation of the resulting classification result (i.e. classification function), it can be enough to check the function values of individual time classes with reference to a predefined threshold value. Another direct evaluation involves, for example, checking the observed extreme values, especially maximum values, of a resulting distribution. According to the present invention, the result of these comparisons then yields the desired conclusion, whether repetitively occurring signal portions of a "noisy" signal can be considered detected or not.

In an additional type of evaluation according to the invention, a resulting distribution can be transformed, for example, by means of a Fourier transform, from the time domain into the frequency domain. In this way, it is possible to acquire an idea of whether and which values of a resulting frequency distribution are present as time-multiples, roughly in the manner of a so-called "cepstrum" analysis.

In special embodiments, the inventive device is characterized by the following partially optional features:

There is a sensor for acquiring machinery noise and for conversion into an electrical signal, and preferably, an analog or digital rectifier for forming the absolute value of the electrical signal.

The device determines, from a signal caused by the machinery noise, special results which are defined in terms of time and intensity.

The device has one, preferably two or more, peak value detectors with different recovery times or decay time constants.

The device has one or more time analyzers for analysis of the output signals of the peak value detectors. In this case, the time analyzers can determine the respective instants of intermediate maximum or minimum values of the electrical signal as time events. The respective time points together with the pertinent signal amplitudes can be stored in a buffer.

The device can form product values from stipulated signal amplitudes of selected time points and can perform frequency analysis.

The device can execute the indicated frequency analysis by time classes which can be essentially freely selected according to predetermined assessment criteria.

The device can undertake frequency analysis using a weighted distribution.

In the execution of frequency analysis for evaluation of a machine or bearing state, the device uses only those events which have a sufficient or significant difference from a noise level.

The device is equipped with a unit for acquisition and proportional subtraction of those functional values which correspond to a multiple of a base time value.

The device is equipped with an evaluation unit by which a frequency measure which belongs to a base time value is evaluated in that whether, what type, and to what extent there is machinery or bearing damage.

The device is equipped with a registration unit with which predefined time values and base time values can be stored over a longer time interval so that at a later time measured in weeks or months, analysis can be performed and a display of the degree of damage for a bearing or for a machine component is possible over greater time intervals.

The device has means with which it is possible to use two or more events of a signal which follow one another directly in time to prepare and store a product or a product sum for the intensities of these events. The products or product sums can be supplied for frequency analysis and subsequent evaluation.

The device has means with which it is possible that relatively large time differences for events can be assumed and processed. The time differences are at least as great as corresponds to a maximum expected repetition time for an event which can be assigned to a special type of damage.

The device can have threshold detectors with decay time constants which agree in terms of order of magnitude with the repetition times or period durations of the effects of the machinery damage or defects to be examined.

The device has means with which a resulting event value is produced by a logic operation from two event intensities at a time (specially defined intensities of the electrical signal) and the logic operation is effected by product formation, by summing, by determining a maximum value or by another relation.

The device can have a means for digital or analog preprocessing of the signal, for rectification or for absolute-value generation of a signal.

The device can have a means for identifying the intermediate extreme values (maximum or minimum values) of the signal. Using such means, an event can be classified according to the instant of its occurrence and its intensity.

For these reasons, the device advantageously has one or more peak value detectors, each of which is characterized by a defined recovery time or decay time constant.

The device has a means for forming and evaluating several frequency distributions in a multiplicity of damage duration categories.

The device can have a selection stage which provides for an event defined in time, triggering or influencing only that peak value detector which is characterized by the time constant which is the largest at the time.

The above described or additional features of the invention can be formulated alternatively or optionally as follows:

The device for detecting or analyzing machinery damage is especially suited for detecting repeated, pulse-like portions of a time-variant signal and especially for recognizing machinery noise which is caused by roller bearing damage, and the device has the following components:

- a sensor, especially in the form of an acceleration sensor, for acquiring and converting the time-variant signal into an electrical AC signal,
- especially at least one filter stage and one signal conversion stage for producing positive definite signal portions, i.e., no negative values result.
- at least one peak value detector stage with preset discharge time constant for detecting the time occurrence of individual relative extreme values (maximum values or minimum values) of the AC signal, a storage unit which stores the times and the intensity (amplitude) of the recognized individual relative extreme values over a predetermined time window (observation interval), a computer which can multiplicatively combine the recognized individual relative extreme values, i.e. their assigned intensities, so that corresponding product values are produced, a classification unit for processing of product values which can compute and store at least one distribution (histogram), furthermore, a pattern recognition unit for analysis of at least one distribution according to preset criteria, especially according to predefined absolute frequency values.

The device can have one or more additional reference signal generators for generating sawtooth reference signals with a steep rise and comparatively slow fall; furthermore, one or more trigger stages for repetitive triggering of the reference signal generators.

The device can have a signal analysis stage in which sampled, time-discrete signals are used to trigger one or more of the trigger stages. These signals can then be compared to the sawtooth reference signals.

The device is able to store different special samples according to their respective instants of occurrence and pertinent signal intensities (amplitude). Furthermore, it has a computer for forming arithmetic products, a classification unit for forming one or more histograms and a pattern recognition unit for classification of histograms according to predetermined criteria.

The device has an analysis unit by which a large number of events can be determined and a large number of logic operations can be sent for histogram analysis until an output by the analysis unit or an evaluation unit according to stipulated statistical criteria can be regarded as being steady-state or statistically relevant.

The device is equipped with one or more comparison stages for checking that stipulated boundary values have—alternatively—been exceeded, have not been reached, or are identical; and the device can have, in particular, a signaling stage. The signaling stage is used for signaling if preset boundary values, filed in the form of histogram values, have been exceeded.

The device can have a digital computer with which time events are determined and with which the data of these events are further processed.

The invention is also based on the finding that the time length of the signals which occur in pulses on the machinery or bearings and which are caused, for example, due to defects or deformation of bearing parts is generally rather short. For this reason, their determination by means of a Fourier transform is difficult due to the other noise components present on a bearing or a machine.

Therefore, according to the invention, it is more advantageous to identify the fraction of pulse-like signal portions per individual event. With these individually determined events, it is then easier to identify the parameters of their occurrence in time. With the data obtained in this way, underlying causes can also be determined in an early stage of damage of machinery or bearings, especially in roller bearings.

However, it is generally not enough to check an individual frequency of the noise spectrum. Rather, e.g. for roller bearings one has to check at least four (4) basic separate frequencies which could indicate damage. These frequencies are referenced, for example, to the dimensions of the inner ring, the outer ring, the rollers and the cage of a roller bearing. Since these frequencies can occur in any combinations, the teaching of U.S. Pat. No. 3,824,663 is only of limited benefit.

With the object of identifying the individual pulse-like noise portions of a faulty machine or bearing, in accordance with the invention, it is provided that these noise portions be analyzed by means of detection for intermediate maximum and minimum values of the acquired and filtered noise signal without the need for a more complex frequency analysis unit, such as a FFT analyzer. One approach according to the invention is to provide one or more peak value detectors which study a prefiltered signal, after its rectification or absolute value generation, for conspicuous time points and the pertinent signal intensities.

Here, it is very advantageous for the individual peak value detectors to have different decay times. In this way, pulse-like noise events, hereinafter simply called events, can be better studied and identified both in different time-scale domains and also in different intensity ranges. According to the invention, it is especially advantageous to study, not individual events and their assigned formation times, but the combination of at least two events which are adjacent in time or apart in time. The combination of at least two events is preferably undertaken such that a multiplicative combination of the two intensity values of the respective events is performed. The statistics to be determined for the product values formed in this way and the pertinent time differences allow conclusions to be drawn about the composition of the repetition times involved, and thus, the nature of underlying machine damage or roller bearing damage. Under certain circumstances, it is enough to study a correspondingly formed frequency distribution or the statistics of the event products over assigned difference times to ascertain whether predefined time domains which can be assigned to one of the aforementioned roller bearing damage frequencies exceed a stipulated threshold or not.

In the invention, it is assumed that it is generally enough to analyze a time interval which comprises only a few to a few hundred seconds. The signals belonging to this time interval can be digitized and stored in a digital memory. Furthermore, in accordance with the invention, it is assumed that a plurality of the described means, functions and processes can be executed not only with analog electronic means, but alternatively or additionally with digital ones, i.e. computer-based. The latter approach then uses the corresponding software for analogous implementation of the means, functions and relationships provided in accordance with the invention.

These and further objects, features and advantages of the present invention will become apparent from the following description when taken in connection with the accompanying drawings which, for purposes of illustration only, show several embodiments in accordance with the present invention.

DETAILED DESCRIPTION OF THE INVENTION

Figure 1:
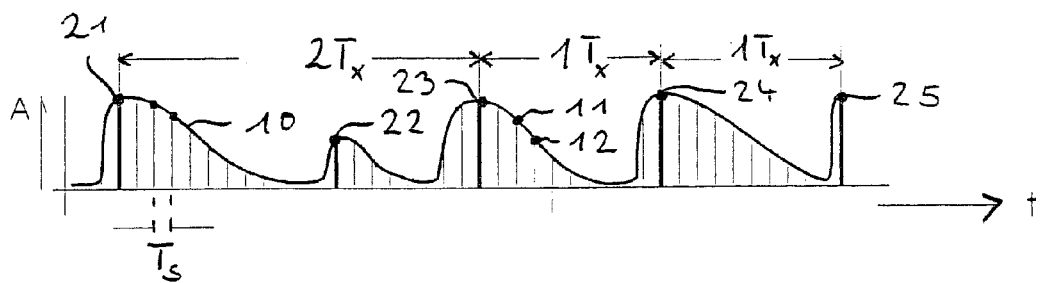
FIG. 1 is a time signal with discrete, positively definite sample values.

The time signal 10 shown in FIG. 1 is present inherently in a positive signal form. If this prerequisite is not present, either only positive or only negative signal components can be examined. It is of special importance according to the invention to make a time signal positive, optionally by absolute value generation or squaring. The time signal 10 is represented for further processing by individual sample values (for example, 11, 12). To do this, conventionally, there is an analog-digital converter (ADC) which samples and digitizes the time signal with a preferably constant sampling time $T_s$. Events 21, 22, 23, 24, 25 which occur more or less regularly are of special interest, particularly in the assessment of machinery noise or in quality analysis of continuously produced products. These events differ by their time difference and also by different intensity values (ordinate A). In the example shown, the time difference values labeled 1 $T_x$ and 2 $T_x$ are especially conspicuous. It is important that the respective, relatively large intensity values, according to the logic operation of the invention, will yield especially large "tallies" with subsequent classification. This applies especially in a logic operation of the multiplicative type.

The signal analysis proposed in accordance with the invention, therefore, works differently than conventional processes. This is, based on the following consideration: When pulse-like signal portions of short duration, but relatively high amplitude compared to the noise level, occur, these signal portions are of special importance, i.e. high information content. They are supplied to the further analysis process by means of increased evaluation factors, and thus, in a nonlinear manner. Consequently, it is necessary to first suitably identify the indicated pulse-like signal portions; this can take place, for example, by recognizing peak values which are examined above a predefined threshold value. If the pulse heights of two such peak values are multiplied by one another, the information content of these two peak values is evaluated to a nonlinear extent. The corresponding value of a product determined in this way, according to the invention, enters with an increased proportion into the frequency distribution which classifies by time differences. Therefore, in a direct approach, these product values are assigned to that time difference class which corresponds to the time difference of the two pulse-like peak values just examined for the usually noisy signal which is to be analyzed.

Figure 2:
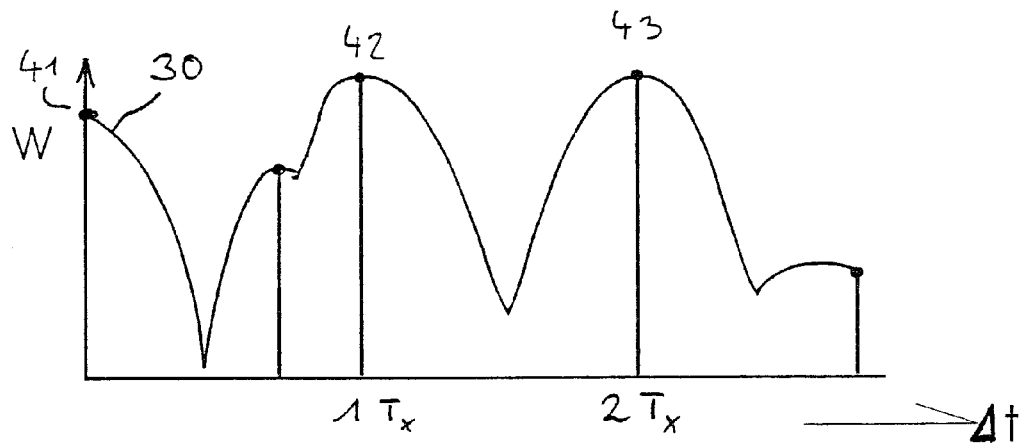
FIG. 2 is a graph of a distribution of the results of logic operations, based on a plurality of sample values.

This circumstance is shown in FIG. 2. The abscissa of the representation corresponds to a time measure. More accurately, time differences "Δt" are specified by the abscissa. A tally W is given versus these time differences. A tally entered at a time difference Δt is based, as described above, for example, on the sum of all product terms found which underlie a correspondingly large time difference. Instead of adding, a respective tally value for a value of Δt can also be determined by an incremental advance, in the manner of a frequency count. A distribution determined by a multiplicative logic operation with the values found and added subsequently is given by reference number 30. For time differences with a value 1 * $T_s$, of course, the frequency values 41 are especially large. Other especially conspicuous values 42, 43 for difference times 1 * $T_x$ and 2*$T_x$ are based on the high intensities in the vicinity of time events 21, 22, 23, 24, 25 by paired product formation leading to correspondingly large portions of the values of the tally function W.

Figure 3:
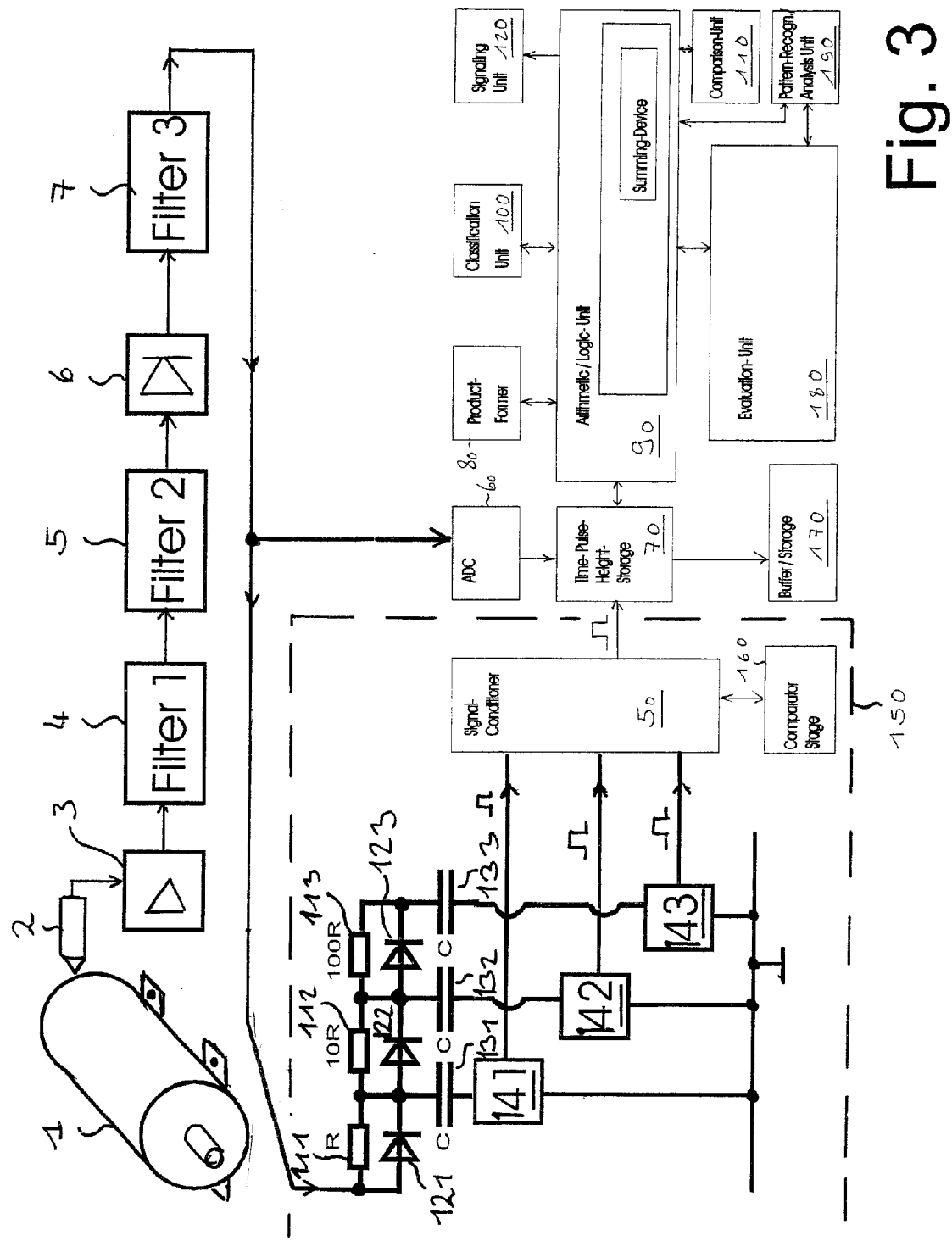
FIG. 3 is a block diagram of a preferred embodiment of the invention.

The block diagram shown in FIG. 3 has a vibration sensor 2 which is attached permanently, or according to the prior art, detachably, to a machine 1. It can be made, for example, as an acceleration sensor which converts mechanical vibrations and noise caused by the machine 1, also especially by its bearings, into an electrical signal. The latter is sent to an amplifier 3 and then to a suitable filter combination, for example, filter 4, 5 having high-pass filters or bandpass filters to filter out high frequency signal portions. This approach and the subsequent rectification or absolute value generation, optionally squaring of the signal, in a rectifier stage 6 are known, likewise the use of an output-connected lowpass stage 7.

From the output of the lowpass stage, which has a comparatively low-resistance output, the signal is sent to a peak value detector unit which contains at least two separate peak value detectors. The three peak value detectors shown in FIG. 3 comprise, for example, the respective R-D-C combinations with a resistor 111, a diode 121, a capacitor 131 and the corresponding components 112, 122, 132 and 113, 123, 133. The diodes 121, 122, 123 shown may have roughly ideal properties. The resistor 113 has a resistance which is, for example, 10 times greater than the resistance value of resistor 112, and for example, 100 times greater than the resistance value of the resistor 111. In this way, different discharge time constants are assigned to the indicated R-D-C combinations. They have a ratio of 1:10:100 in the example shown. Therefore, signal voltages which correspond to the peak values of the signal values which have reached a maximum in the interim can be tapped on the capacitor terminals which are not connected against the reference potential. Based on the different charging time constants, however, larger peak voltages are recorded on the larger RC combinations, as is explained in the description of FIG. 4, below.

The peak values tapped on the indicated terminals are, therefore, with greater probability, an indicator of a noise event which has a pulse-like nature and with the corresponding probability originates from repetitive machinery damage. As FIG. 3 shows, according to the invention, a plurality of suitable peak value detectors determines not only events with especially great intensity, but also those with a smaller intensity.

In order to determine the respective instant of occurrence of individual peak voltage values on the capacitors, according to the embodiment shown in FIG. 3, between the capacitor and reference potential line, a zero current detector 141, 142, 143 or differentiator is connected. Its output signals are essentially pulse-shaped or have at least one steep edge. These pulse-like signals are optionally combined by a signal conditioning stage 50 or are relayed directly to a time-pulse height storage unit 70.

With the time-pulse height storage unit 70, on the one hand, instants are recorded which can be assigned to the occurrence of the described peak voltage values. On the other hand, at the same time, the pertinent actual pulse heights of the signal delivered by the filter 3 (reference number 7 in FIG. 3) are determined by a suitable means, for example, an analog-digital converter 60. In this way, over a predetermined time interval, for example, 1 to 10 seconds, a plurality of data are acquired which are possibly the result of machinery or bearing damage, and which provide information both on the instants of occurrence and also the intensities of these signals.

It is advantageous to provide preferably digital means for the time-pulse height storage 70. The time-pulse height storage 70 can also be designed as a ring storage so that the characteristics of the signal which are oldest at the time are overwritten with those of the current, most recent signal.

In any case, the data of a filled time-pulse height storage 70 are used to produce special product values. To do this, the intensity value for each recorded event (except for the first) is multiplied by that of the one recorded previously. To do this a multiplier 80 is used. The corresponding product value and the underlying time difference are sent to distribution analysis. This takes place as follows: A classification unit 100 has individual registers which are assigned to defined time classes, for example, 400 time classes with the same (or different) width.

Individual register contents can be changed, therefore, depending on an observed or current time value, for example, by incrementing (increasing its value by a value of 1) or by summing (increasing its value by a summand, especially a summand made available by product formation).

Since, for the aforementioned formed products, the value of the respectively pertinent time difference is also known, depending on this time difference, a respective corresponding register of the classification unit 100 is increased by summing, preferably by summing by the value of the product.

In the different registers of the classification unit 100, therefore, by storing a plurality of individual products, a distribution (histogram) is mapped quantitatively. If all values are stored, special classes or registers of the distribution will have significantly higher values compared, for example, to the average of all classes.

In one modification of the process, the formation of intensity products is performed similarly, but with the difference that the preceding event values or pulse height values are not used as the multiplier, but their predecessors, etc.

However, to assign a formed product to the distribution by means of the classification unit, in turn, that underlying time difference is used which was filed in the time-pulse height storage 70 for the corresponding multipliers and multiplicands.

When the arithmetic/logic unit 90 has created all of the products to be formed by means of a multiplier 80 and sent them to the classification unit 100, it is ascertained with the comparison unit 110 which time classes of the classification unit 100 are most heavily occupied, therefore, are characterized by the largest function or frequency values. Furthermore, it is ascertained whether they differ significantly from the average of the values.

It is pointed out that the above described computation process works exclusively with arguments of the time domain. Nor is product formation with trigonometric functions performed. By this measure and the limitation to multiplication terms with special information content, otherwise necessary computing power or time is saved.

For a machine 1, if its rotational frequency (rpm) and its rolling bearing parameters are known, according to the known formulas, it can be predicted which repetition times or frequencies can be expected for which bearing damage. According to the invention, it is therefore possible to check by means of the comparison unit 110 those time classes which are filed in the classification unit 100 and which correspond to the repetition times which are caused by specific bearing damage. Furthermore, it is of interest to check those time classes which correspond to a multiple of these predetermined repetition times.

If, in one or more of these classes, a frequency value is ascertained which is greater than one defined previously, or which differs from the average of the frequencies with a stipulated significance, this can be interpreted as an indicator for incipient or existing bearing damage. In this case, the arithmetic/logic unit 90 can activate a external signaler, for example, a signal lamp 120.

It may be stated that the combination of peak detectors as depicted by reference numerals 1xy (x counting from 1 to 4, y counting from 1 to 3), signal conditioning unit 50 and comparator(s) 160 form a selection unit 150.

Figure 4:
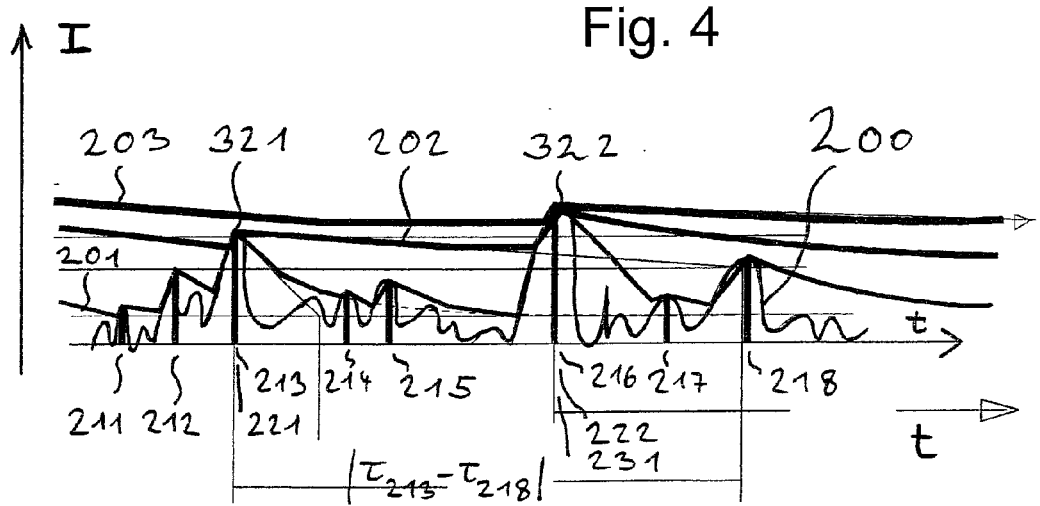
FIG. 4 is a pulse diagram for explanation of the process in accordance with the invention.

FIG. 4 shows the output signals of the individual peak value detectors and the time variation of the respective signal functions.

The signal tapped at the output of the filter 3 is positive and in FIG. 4 is labeled with reference number 200.

The signal generated by the peak value detector 111, 121, 131 has a comparatively small time constant and is identified by reference number 201.

As is apparent from FIG. 4, the signal 201 is carried or raised by the signal function 200 up to the intermediate maximum values for time values 211, 212, etc., to then drop towards a value of zero with a predetermined time constant, until repeated carrying up to a subsequent peak value takes place. As is apparent, in this way, intermediate maximum values with relatively low intensity are also specified and identified. Accordingly, the average value of the signal 201 is also comparatively small.

Similarly, the signal from peak value detector 112, 122, 132 identified by the reference number 202 is raised only at times 221 (=213), 222(=216) by the triggering signal function up to corresponding intermediate maximum values 321, 322 in order to subsequently drop with its preset time constants. This time drop in the example shown is essentially exponential, but can also have a linear behavior or according to another stipulated, especially monotonically decreasing time function.

Similarly the signal from peak value detector 113, 123, 133 identified by the reference number 203 is raised only at time 231 (=222, =216) by the triggering signal function up to its intermediate maximum value with the peak value.

Since the time constant underlying the signal 203 is greater than that of signal 201 and the signal 202, this signal 203 represents only a few marked values which, however, are characterized by a comparatively high intensity.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

I claim:

1. Device for signal analysis comprising:
    a sampling and conversion means for forming sample values of a signal, and for digitizing the sample values;
    a selection unit for selecting specific sample values;
    an arithmetic-logic operation unit having means for combining a pair of selected specific sample values according to a defined relation and for outputting resultant values; and
    classification means connected to receive the resultant values from the arithmetic-logic operation unit for classifying the resultant values and producing a distribution of the resultant values, which distribution is based on distances that separate each combined pair of sample values;
    an evaluation unit for evaluating a distribution of said resultant values obtained from the classification means; and,
    computational means for determining a significant frequency value, an integral multiple of a time difference value assigned to the significant frequency value, and for determining frequency values of the integral multiple of time difference values; and wherein the evaluation unit has an evaluation means for the frequency values.

2. Device according to claim 1, wherein said means for combining has means for producing a summation of sample values; and wherein said distribution produced by the classification means is a frequency distribution of the values formed by summation.

3. Device as claimed in claim 1, wherein said evaluation unit evaluates the classification results for detection or analysis of machinery damage.

4. Device as claimed in claim 3, wherein said evaluation unit is functionally connected to a comparison unit for evaluating the classification results for detection of roller bearing defects.

5. Device for detection or for analysis of machinery damage or defects which cause noise, with determined and stochastic properties, comprising:
- a sensor for acquiring machinery noise and for conversion of said noise into an electrical signal;
- a rectifier for forming an absolute value of the electrical signal;
- at least one peak value detector; and
- at least one time analyzer for analysis of output signals of the at least one peak value detector for determining of special events, defined by time and intensity, from said electrical signal, wherein the at least one time analyzer has means for determining respective instants of intermediate maximum and minimum values of a signal function as time events; and wherein a buffer storage is provided for storing the respective instants together with the respective signal amplitudes.

6. Device according to claim 5, wherein said at least one peak detector comprises at least two peak detectors, each peak detector having a different recovery time or decay time constant.

7. Device as claimed in claim 5, wherein a multiplier is provided for producing product values from stored respective instants representing time events at predetermined time differences and signal amplitudes of the signal function; and wherein means for subjecting the product values to frequency analysis is provided.

8. Device as claimed in claim 7, further comprising an unit for acquisition and proportional subtraction of time values which correspond to a multiple of a base time value.

9. Device as claimed in claim 7, further comprising an evaluation unit for evaluating the frequency analysis and for determining whether, what type, and to what extent machinery damage is reflected in the electrical signal.

10. Device as claimed in claim 5, further comprising a registration unit for storing selected time and intensity values over a longer time interval than provided by said buffer storage for enabling long term recording and analysis of machinery component damage.

11. Device as claimed in claim 5, comprising a logic operation unit for producing an event value from two event intensities at a time by one of product forming, summing, and maximum value determining.

12. Device as claimed in claim 5, wherein a means for at least one preprocessing, rectification and absolute-value generation of said electrical signal is provided.

13. Device as claimed in claim 5, further comprising evaluation means for forming and evaluating several frequency distributions in a multiplicity of damage duration categories.

14. System for detecting repeated, pulse-like signal portions of a time signal comprising
- a sensor for acquiring and converting a time signal into an electrical AC signal;
- an electronic sampling means for sampling the AC signal and for generating a sampled, time discrete signal;
- at least one reference signal generator for generating sawtooth reference signals with a steep rise and comparatively slow fall;
- at least one trigger stage for repetitive triggering of the reference signal generators;
- a signal analysis stage which uses scanned, time-discrete signals for triggering the at least one trigger stage and which has means for comparing the sampled, time-discrete signals to the sawtooth reference signals;
- a storage unit for storing special sample values with respect to an instant of their occurrence and an amplitude thereof;
- an arithmetic unit for forming arithmetic products;
- a classification unit for forming at least one histogram; and
- a pattern recognition unit for classification of histograms according to predetermined criteria.

15. System according to claim 14, further comprising a signal conversion means for producing positive definite signal portions, and at least one filter means.

16. System as claimed in claim 14, further comprising an analysis unit for determining a number of events and sending a number of events combined with one another for histogram analysis until an event or an evaluation of the histogram analysis is determined to reflect a steady-state condition.

17. System as claimed in claim 14, further comprising an analysis unit for determining a number of events and sending a number of events combined with one another for histogram analysis until an event or an evaluation of the histogram analysis is determined to be statistically relevant according to predetermined criteria.

18. System as claimed in claim 14, further comprising at least one comparison stage for checking that predetermined limit values have been exceeded, have not been reached, or have been equaled; and a signaling stage for outputting a signal if values filed in the histogram exceed the predetermined limit values.

19. System as claimed in claim 14, further comprising a comparator stage and a digital arithmetic unit for generating time-variable threshold signals which are sent to the comparator stage for use as comparison signals for determining time events.

20. Process for signal analysis comprising the steps of
- using a sampling and conversion means for forming sample values of a signal;
- digitizing the signal;
- combining each sample value in a logic operation unit, which combines each sample value of a signal with a plurality of the sample values of the signal, using a logic operation performed according to one of product formation, sum formation, and maximum formation of at least two relative maximum values of the signal;
- sending the results of the logic operation for classification by means of a classification unit, and performing classification in the manner of a distribution; and
- using an evaluation unit for evaluation of one of a classification result and a distribution of frequency distribution, wherein said evaluation is performed using the further steps of determining a significant frequency value, determining an integral multiple of a time difference value which is assigned to the significant frequency value, determining frequency values at integral multiple of time difference values; and evaluating the frequency values determined.

21. Process as claimed in claim 20, further comprising the step of determining the existence of machinery damage from said evaluation.

22. Process as claimed in claim 21, wherein the machinery damage determined is the existence of roller bearing defects.

* * * * *